US00PP25180P2

(12) United States Plant Patent
Noordhuis

(10) Patent No.: US PP25,180 P2
(45) Date of Patent: Dec. 16, 2014

(54) ***LIRIOPE* PLANT NAMED 'ET-LIR 1'**

(50) Latin Name: *Liriope muscari*
Varietal Denomination: ET-LIR 1

(71) Applicant: Bart Noordhuis, Boijl (NL)

(72) Inventor: Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 81 days.

(21) Appl. No.: 13/815,331

(22) Filed: Feb. 21, 2013

(51) Int. Cl.
*A01H 5/00* (2006.01)

(52) U.S. Cl.
USPC ..... Plt./450

(58) Field of Classification Search
USPC ..... Plt./450
See application file for complete search history.

*Primary Examiner* — Annette Para
(74) *Attorney, Agent, or Firm* — C. A. Whealy

(57) ABSTRACT

A new and distinct cultivar of *Liriope* plant named 'ET-LIR 1', characterized by its upright to outwardly arching plant habit with long, strong, upright flowering stems; freely flowering habit; large dark violet-colored flowers; good garden performance; and winter hardiness.

2 Drawing Sheets

Botanical designation: *Liriope muscari*.
Cultivar denomination: 'ET-LIR 1'.

BACKGROUND OF THE INVENTION

The present invention relates to a new and distinct cultivar of *Liriope* plant, botanically known as *Liriope muscari* and hereinafter referred to by the name 'ET-LIR 1'.

The new *Liriope* plant is a product of a planned breeding program conducted by the Inventor in Boijl, The Netherlands. The objective of the breeding program is to create new freely-flowering *Liriope* plants with long-lasting flowers on strong flowering stems.

The new *Liriope* plant originated from a cross-pollination made by the Inventor in Boijl, The Netherlands in September, 2007 of a proprietary selection of *Liriope muscari* identified as code number 1-684, not patented, as the female, or seed parent with a proprietary selection of *Liriope muscari* identified as code number 4-756, not patented, as the male, or pollen, parent. The new *Liriope* plant was discovered and selected by the Inventor as a single flowering plant from within the progeny of the stated cross-pollination in a controlled environment in Boijl, The Netherlands in August, 2008.

Asexual reproduction of the new *Liriope* plant by divisions in a controlled environment in Boijl, The Netherlands since March, 2009 has shown that the unique features of this new *Liriope* plant are stable and reproduced true to type in successive generations.

SUMMARY OF THE INVENTION

Plants of the new *Liriope* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'ET-LIR 1'. These characteristics in combination distinguish 'ET-LIR 1' as a new and distinct *Liriope* plant:

1. Upright to outwardly arching plant habit with long, strong, upright flowering stems.
2. Freely flowering habit.
3. Large dark violet-colored flowers.
4. Good garden performance; winter hardy.

Plants of the new *Liriope* differ from plants of the female parent selection in the following characteristics:

1. Leaves of plants of the new *Liriope* are broader than leaves of plants of the female parent selection.
2. Plants of the new *Liriope* are more freely flowering than plants of the female parent selection.
3. Inflorescences of plants of the new *Liriope* are positioned higher above the foliar plane than inflorescences of plants of the female parent selection.

Plants of the new *Liriope* differ from plants of the male parent selection in the following characteristics:

1. Leaves of plants of the new *Liriope* are broader than leaves of plants of the male parent selection.
2. Plants of the new *Liriope* are more freely flowering than plants of the male parent selection.
3. Inflorescences of plants of the new *Liriope* are positioned higher above the foliar plane than inflorescences of plants of the male parent selection.

Plants of the new *Liriope* can be compared to plants of *Liriope muscari* 'ET-LIR 2', disclosed in a U.S. Plant Patent application filed concurrently. Plants of the new *Liriope* and 'ET-LIR 2' differ in the following characteristics:

1. Leaves of plants of the new *Liriope* are broader and darker green in color than leaves of plants of 'ET-LIR 2'.
2. Flowers of plants of the new *Liriope* are darker violet in color than flowers of plants of 'ET-LIR 2'.

Plants of the new *Liriope* can also be compared to plants of *Liriope muscari* 'Moneymaker', not patented. In side-by-side comparisons conducted in Boijl, The Netherlands, plants of the new *Liriope* differed primarily from plants of 'Moneymaker' in the following characteristics:

1. Plants of the new *Liriope* were taller and broader than plants of 'Moneymaker'.

2. Leaves of plants of the new *Liriope* were larger and darker green in color than leaves of plants of 'Moneymaker'.
3. Plants of the new *Liriope* were more freely flowering than plants of 'Moneymaker'.
4. Flowers of plants of the new *Liriope* were darker in color than flowers of plants of 'Moneymaker'.
5. Plants of the new *Liriope* were more winter hardy than plants of 'Moneymaker'.

BRIEF DESCRIPTION OF THE PHOTOGRAPHS

The accompanying colored photographs illustrate the overall appearance of the new *Liriope* showing the colors as true as it is reasonably possible to obtain in colored reproductions of this type. Colors in the photographs may differ slightly from the color values cited in the detailed botanical description which accurately describe the colors of the new *Liriope*.

The photograph on the first sheet comprises a side perspective view of a typical flowering plant of 'ET-LIR 1'.

The photograph on the second sheet is a close-up view of a typical flowering plant of 'ET-LIR 1'.

DETAILED BOTANICAL DESCRIPTION

The aforementioned photographs and following observations, measurements and values describe plants grown in containers during the late summer and autumn in an outdoor nursery in Boijl, The Netherlands and under cultural conditions typical of commercial *Liriope* production. During the production of the plants, day temperatures ranged from 15° C. to 25° C. and night temperatures ranged from 10° C. to 15° C. Plants were three years old when the photographs and the detailed description were taken. In the following description, color references are made to The Royal Horticultural Society Colour Chart, 2001 Edition, except where general terms of ordinary dictionary significance are used.

Botanical classification: *Liriope muscari* 'ET-LIR 1'.

Parentage:

*Female, or seed, parent*.—Proprietary selection of *Liriope muscari* identified as code number 1-684, not patented.

*Male, or pollen, parent*.—Proprietary selection of *Liriope muscari* identified as code number 4-756, not patented.

Propagation:

*Type*.—By divisions.

*Time to initiate roots, summer*.—About four weeks at temperatures about 15° C. to 20° C.

*Time to initiate roots, winter*.—About four weeks at temperatures about 5° C. to 10° C.

*Time to produce a rooted young plant, summer*.—About ten weeks at temperatures about 15° C. to 20° C.

*Time to produce a rooted young plant, winter*.—About ten weeks at temperatures about 5° C. to 10° C.

*Root description*.—Medium in thickness, fibrous.

*Rooting habit*.—Freely branching; medium density.

Plant description:

*Plant form and growth habit*.—Herbaceous flowering perennial plant; upright plant habit with outwardly arching foliage with upright, strong and long flowering stems; flowering stems and leaves basal; moderately vigorous growth habit; moderate growth rate.

*Plant height (soil level to top of inflorescences)*.—About 40 cm to 50 cm.

*Plant width (spread)*.—About 40 cm to 50 cm.

Foliage description:

*Arrangement*.—Basal rosette, simple, sessile.

*Length*.—About 20 cm to 50 cm.

*Width*.—About 1 cm to 2 cm.

*Shape*.—Acicular.

*Apex*.—Obtuse to acute.

*Base*.—Decurrent.

*Margin*.—Entire.

*Texture, upper and lower surfaces*.—Rough, glabrous.

*Venation pattern*.—Parallel.

*Color*.—Developing and fully developed leaves, upper surface: Close to 139A; venation, close to 136A. Developing and fully developed leaves, lower surface: Close to 136B, venation, close to 136A.

Flower description:

*Flower type and flowering habit*.—Numerous single flowers arranged on dense terminal racemes; flowers face outwardly; freely flowering habit; about 150 to 200 flowers per inflorescence.

*Fragrance*.—None detected.

*Natural flowering season*.—Plants begin flowering about 15 weeks after planting; in the garden, plants flower continuously from late summer to late autumn in The Netherlands.

*Postproduction longevity*.—Flowers last about eight to ten weeks on the plant; flowers persistent.

*Flower buds*.—Height: About 4 mm to 6 mm. Diameter: About 2 mm to 3 mm. Shape: Oval to obovate. Color: Close to 86A.

*Inflorescence height*.—About 15 cm to 20 cm.

*Inflorescence diameter*.—About 2.5 cm to 3 cm.

*Flower diameter*.—About 5 mm to 7 mm.

*Flower depth*.—About 6 mm to 8 mm.

*Perianth*.—Three inner segments arranged in a single whorl and three outer segments in a single whorl; segments separate. Inner segments: Length: About 5 mm. Width: About 3 mm. Shape: Elliptic. Apex: Obtuse. Base: Obtuse. Margin: Entire. Texture, upper and lower surfaces: Smooth, glabrous. Color: When opening and fully opened, upper surface: Close to 86A; color does not fade with development. When opening and fully opened, lower surface: Close to 86B; color does not fade with development. Outer segments: Length: About 4 mm to 6 mm. Width: About 2 mm to 3 mm. Shape: Lanceolate. Apex: Obtuse. Base: Obtuse. Margin: Entire. Texture, upper and lower surfaces: Smooth, glabrous. Color: When opening and fully opened, upper surface: Close to 86A; color does not fade with development. When opening and fully opened, lower surface: Close to 86B; color does not fade with development.

*Peduncles*.—Length: About 40 cm to 50 cm. Diameter: About 1 cm. Angle: Mostly upright. Strength: Strong. Texture: Smooth, glabrous. Color: Close to N186A; towards the apex, becoming closer to 76A.

*Pedicels*.—Length: About 3 mm to 5 mm. Diameter: About 1 mm to 2 mm. Angle: About 90° from the inflorescence stalk. Strength: Weak to moderately strong. Texture: Smooth, glabrous. Color: Close to 86D.

*Reproductive organs*.—Stamens: Quantity per flower: Typically six. Filament length: About 1 mm. Filament color: Close to 86C. Anther shape: Lanceolate to elliptic. Anther length: About 1 mm to 2 mm. Anther color: Close to 6A. Pollen amount: None observed.

Pistils: Quantity per flower: One. Pistil length: About 2 mm. Style length: About 2 mm. Style color: Close to 86C. Stigma shape: Round. Stigma color: Close to N88C. Ovary color: Close to 86C.

*Seeds and fruits*.—Seed and fruit development have not been observed on plants of the new *Liriope*.

Disease & pest resistance: Plants of the new *Liriope* have not been noted to be resistant to pathogens and pests common to *Liriope* plants.

Garden performance: Plants of the new *Liriope* have been observed to have good garden performance and to tolerate rain, wind and temperatures from about −25° C. to about 40° C.

It is claimed:

1. A new and distinct *Liriope* plant named 'ET-LIR 1' as illustrated and described.

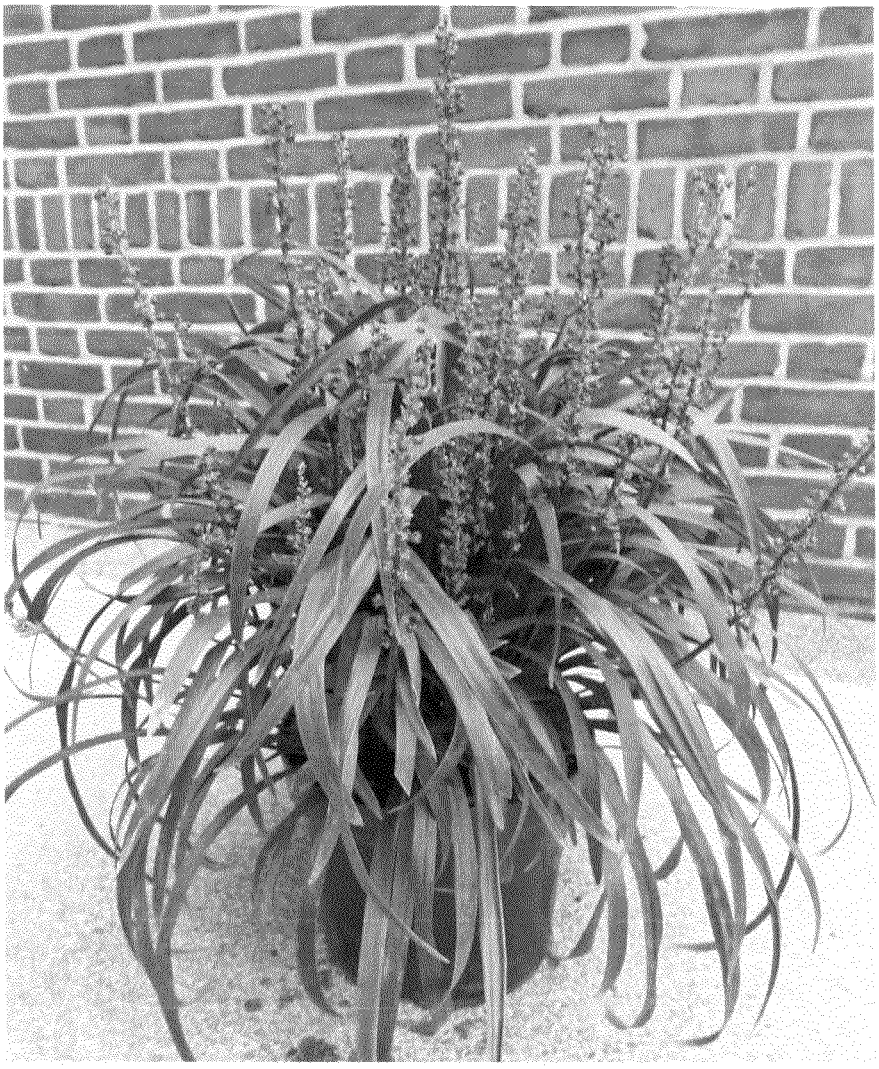

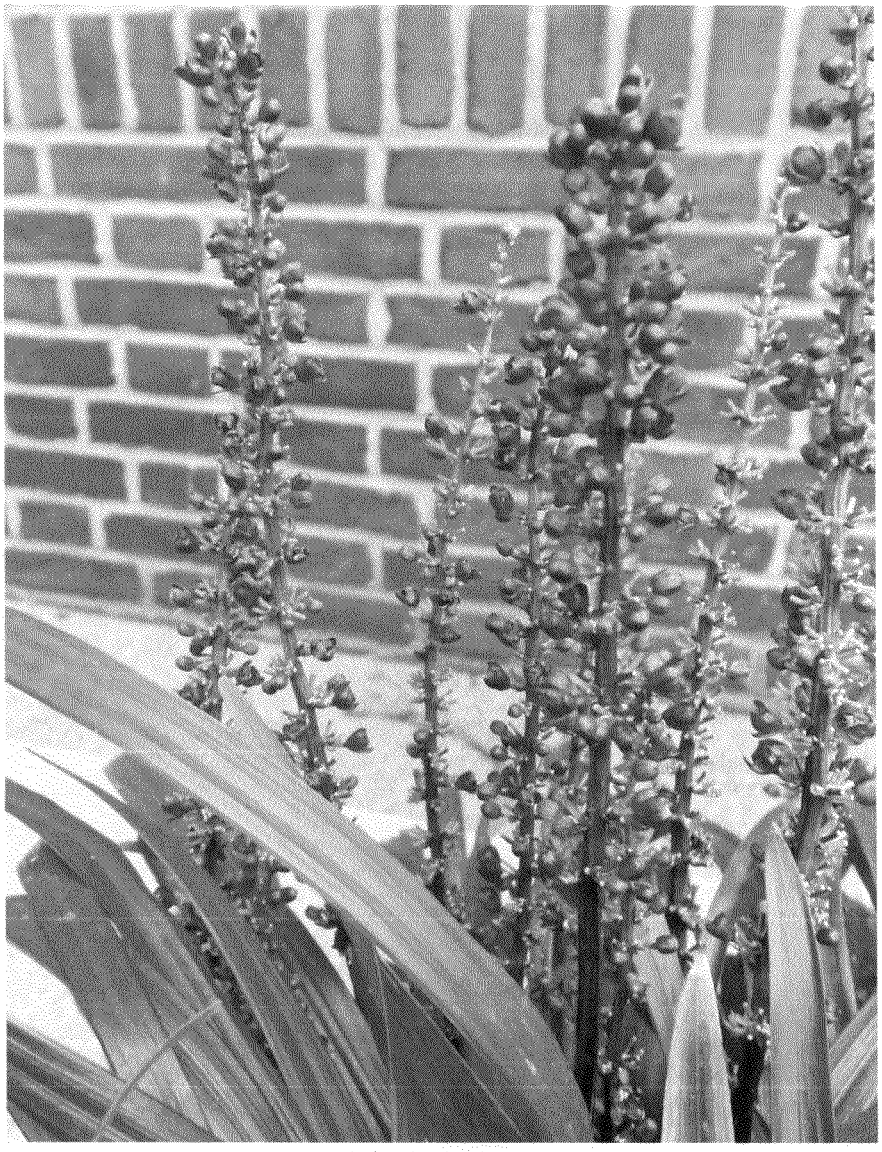

* * * * *